United States Patent [19]

Muchowski et al.

[11] Patent Number: 4,548,949

[45] Date of Patent: Oct. 22, 1985

[54] +2-[(3,4-METHYLENEDIOXY)PHENE-THYL]-5-[(3-CARBOXAMIDO-4-HYDROXY)-α-HYDROXYBENZYL]PYRROLIDINES

[75] Inventors: Joseph M. Muchowski, Sunnyvale, Calif.; Robert Greenhouse, Mexico City, Mexico; Jack Ackrell, Palo Alto, Calif.; Tsung-Tee Li; Jurg R. Pfister, both of Los Altos, Calif.

[73] Assignee: Syntex (U.S.A.) Inc., Palo Alto, Calif.

[21] Appl. No.: 527,716

[22] Filed: Aug. 29, 1983

Related U.S. Application Data

[63] Continuation-in-part of Ser. No. 460,204, Jan. 24, 1983, abandoned, which is a continuation-in-part of Ser. No. 285,892, Jul. 22, 1981.

[51] Int. Cl.⁴ .................... C07D 405/06; A61K 31/40
[52] U.S. Cl. ..................................... 514/422; 548/526
[58] Field of Search .................... 548/526; 424/274

[56] References Cited

U.S. PATENT DOCUMENTS 4,342,692  8/1982  Suh et al. .......................... 548/526

Primary Examiner—Glennon H. Hollrah
Assistant Examiner—D. B. Springer
Attorney, Agent, or Firm—Ellen J. Buckles; Tom M. Moran; Alan M. Krubiner

[57] ABSTRACT

A compound of the formula

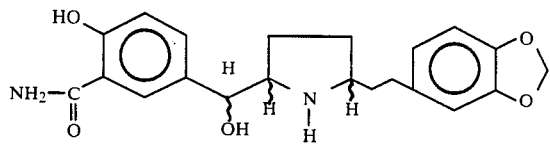

and the pharmaceutically acceptable acid addition salts thereof are potent antihypertensive agents and are therefore useful as cardiovascular system regulators. These compounds are also useful as bronchodilators.

9 Claims, No Drawings

±2-[(3,4-METHYLENEDIOXY)PHENETHYL]-5-[(3-CARBOXAMIDO-4-HYDROXY)-α-HYDROXYBENZYL]PYRROLIDINES

This application is a continuation-in-part of application Ser. No. 460,204, filed Jan. 24, 1983, abandoned which is a continuation-in-part of application Ser. No. 285,892, filed July 22, 1981.

BACKGROUND OF THE INVENTION

1. Field of the invention

This invention concerns ±2-[(3,4-methylenedioxy)-phenethyl]-5-[(3-carboxamido-4-hydroxy)-α-hydroxybenzyl]pyrrolidines which affect the cardiovascular system and which are particularly effective as antihypertensive agents. The invention is directed mainly toward orally active, long lasting cardiovascular regulators of hypertension. However, the compounds of this invention are also potent bronchodilators.

The invention is also directed toward pharmaceutical compositions useful for management of hypertension and toward the method of use for regulating the cardiovascular system in mammals.

2. Related Disclosures

The invention herein concerns cyclic analogs of compounds known to possess molecular segments which affect peripheral nervous system receptors regulating the cardiovascular system. These compounds are also effective as bronchodilators.

Various physiological responses result from administering pharmaceuticals which affect the cardiovascular system regulating receptors. These responses may vary from vasodilation, vasoconstriction, tachycardia, bradycardia, positive or negative inotropic effect. Secondary effects such as bronchodilation or bronchoconstriction can also appear.

The physiological response depends on the exact nature of the drug. Therefore, various members of the same general class of compounds may be used in the treatment of cardiac disorders such as hypertension, cardiac arrhythmia, and vasal congestion.

The following resume represents a compilation of the known compounds which most closely resemble, in molecular structure, the compounds of the present invention, and which are useful in treating cardiovascular disorders and in other therapeutic applications.

Practolol and prenalterol which are amino-alcohol aryl ethers are well known and commercially available compounds which affect the $\alpha_1$ adrenergic receptors of the peripheral system.

Sulfinolol, (British Pat. No. 1,544,872, published Apr. 25, 1979) and its relatives, are known antihypertensive/antiarrhythmic agents.

Deliberate attempts to combine $\alpha_1$ affectors with vasodilators resulted in compounds such as naphthalenone phthalazinylhydrazones. Naphthalenone phthalazinylhydrazones may be hydrolyzed in the body to form a well known peripheral vasodilator hydralazine, and a general α adrenergic blocker bunolol, (see U.S. Pat. No. 4,061,636).

Cyclic compounds containing a 5 or 6 membered saturated nitrogen-containing ring, linked through a hydroxymethyl group to an aromatic nucleus, such as, for example, rimeterol (Pinder, R. M. et al, *Drugs*, 14:81 (1977)) and other compounds disclosed in European Pat. No. 10460, published Apr. 30, 1980 are known psychotropic and hypolipaemic agents. Rimeterol, itself, is a known $\alpha_2$ agonist which is effective when given parentherally, but not effective when administered orally. Some of these compounds have recently been described as having hypotensive effect (See European Pat. No. 22408).

British Pat. No. 1,392,674, published Apr. 30, 1975, discloses compounds related in structure to those of the current invention which are useful for treatment of acute slowdown cardiac contractility.

U.S. Pat. No. 4,342,692 and its EPO counterpart disclose a family of compounds which may be interpreted to be similar to the compounds of the current invention. U.S. Pat. No. 3,655,693 discloses salicylic acid derivatives useful in the treatment of inflammation. U.S. Pat. No. 3,984,200 discloses mono or dihydroxyphenylalkyl dopamine derivatives useful as inotropic agents.

The present invention is directed toward orally active, long acting cardiovascular regulators. The compounds combine, in a sterically controlled way, two segments related to structures showing analogous activities (i.e. an arylhydroxymethyl or benzyl moiety bridged through a short chain to nitrogen and another aromatic group also linked to a nitrogen), by joining these through a common nitrogen atom cyclized to form a pyrrolidine ring.

The compound of this invention have a strong antihypertensive activity. The antihypertensive activity of the compounds of this invention is best shown by their effect on the systolic blood pressure. The compounds of this invention decrease significantly the systolic blood pressure without at the same time increasing heart rates. Moreover, the dosage which is needed to decrease systolic blood pressure is very low and the secondary, often undesirable, side effects are thus avoided. Thus, this invention offers the effective management of hypertension without submitting the treated subject to the undesirable secondary effects which would be unavoidable if large doses are needed.

SUMMARY OF THE INVENTION

One aspect of this invention relates to compounds of the formula

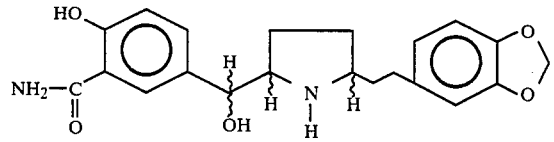

and their pharmaceutically acceptable acid addition salts. These compounds are potent antihypertensive agents and are therefore useful as cardiovascular system regulators.

The other aspect of this invention relates to the mixture of and to individual stereoisomers, namely cis erythro, cis threo, trans erythro and trans threo isomers of the above compounds.

Yet another aspect relates to the method of use of the compounds of this invention as cardiovascular regulators and to the pharmaceutical composition useful in regulating cardiovascular disorder, particularly in managing hypertension.

DETAILED DESCRIPTION OF THE INVENTION

Definitions

As used hereinafter:

"Noble metal catalyst" is a catalyst such as platinum on carbon, platinum oxide, palladium on carbon, or rhodium on carbon, but other noble metal catalysts suitable to effect catalytic reductions are also included.

"Protection" or "Protecting group" refer to the protection of phenolic hydroxyl groups. A phenolic hydroxyl group is present in compounds prepared by the process of this invention. In order to preserve the phenolic hydroxyl group during the catalytic reduction, O-protection is often required for phenols, which react readily with oxidizing agents, electrophiles, or even with mild alkylating and acylating agents. The protection of phenolic hydroxyl groups can be achieved with any suitable protecting group such as an alkyl ether, for example methyl ether, isopropyl ether, t-butyl ether; alkoxymethyl ether, for example methoxymethyl ether; alkoxyethoxymethyl ether, for example methoxyethoxymethyl ether; cycloalkylmethyl ether, for example cyclopropylmethyl ether; alkyldimethylsilyl ether, for example t-butyldimethylsilyl ether, 9-anthrylmethyl ether, preferably substituted or unsubstituted benzyl ether. [*Protective Groups in Organic Synthesis*, John Wiley & Sons, New York, pp:87-100(1980); Synthesis, (II): 987 (1982)].

"N-Protection" or "N-Protecting groups" refer to electron withdrawing groups which make pyrrole less aromatic and more susceptible to the reduction. Electron withdrawal achieved through the utilization of N-protection of the nitrogen atom of the pyrrole can be best illustrated by attachment of the acyl N-protecting group, i.e.

where R may be aryl, phenyl, substituted phenyl, alkyl of 1-4 carbons with branched alkyl preferred, alkoxy of 1-4 carbons with branched alkoxy preferred. Exemplary N-protecting groups for the pyrrole nitrogen atom are alkoxycarbonyl such as methoxycarbonyl, ethoxycarbonyl, propoxycarbonyl, t-butoxycarbonyl and the like, or alkylcarbonyl such as methylcarbonyl, ethylcarbonyl, propylcarbonyl and the like, or alkanoyl such as ethanoyl, propanoyl, butanoyl and the like, or aroyl.

"Aroyl" means the radical ZCO— wherein Z is an aromatic group such as, for example, benzoyl or naphthoyl.

"Wt %" (weight percent) used for solids means the weight of one solid relative to the total weight of all reactants. For example, if 10 wt % of catalyst is given, then 10 g of catalyst are added for 90 g of other reactants.

"Mild reaction conditions" means that the reaction is run at the low temperature between 10°-35° C., preferably ambient and at pressures of 1-5 atmospheres, preferably at atmospheric pressure, in the presence of a suitable organic solvent.

"Organic solvent" means liquid organic compound with the power to dissolve solids or liquids at mild reaction conditions. The term is meant to include cyclic and acyclic compounds such as alcohols of 1-4 carbons, lower alkyl ester of alkanoic acids, ethers, cyclic ethers and the like. Examplary solvents are methanol, ethanol, ethyl acetate, tetrahydrofuran, benzene or mixtures thereof.

"Lower alkyl" means a branched or unbranched saturated hydrocarbon chain containing from one to four carbon atoms, such as, for example, methyl, ethyl, n-propyl, iso-propyl, n-butyl, iso-butyl and the like.

"Cycloalkyl" means a saturated monocyclic hydrocarbon of 3-7 carbons without side chains, such as cyclopropane, cyclobutane, cyclopentane, cyclohexane and cycloheptane.

"Alkoxy" means —OR wherein R is lower alkyl as defined hereinabove.

"Alkoxycarbonyl" means —C(O)—OR wherein R is lower alkyl as defined hereinabove.

"Alkylcarbonyl" means —C(O)—R wherein R is lower alkyl as defined hereinabove.

Hereinafter "α-hydroxybenzyl" or "phenylhydroxymethyl" mean compounds of the formula

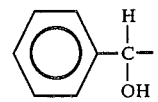

"Strong acid" means an organic or inorganic, water soluble, easily dissociable Bronsted Lowry acid, such as methanesulfonic, trifluoroacetic, hydrochloric, sulfuric, phosphoric acid and the like.

"Strong base" means an inorganic, water soluble base such as sodium hydroxide, sodium carbonate, potassium carbonate, and the like.

"N-acylating" means the formation or introduction of acyl radical

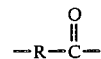

to the N-atom of the pyrrole ring.

"Ph" in Reaction Schemes drawings means phenol.

STEREOCHEMICAL CONTROL

The ±2-[(3,4-methylenedioxy)phenethyl]-5-[(3-carboxamido-4-hydroxy)-α-hydroxybenzyl]pyrrolidines have three chiral centers. Two chiral centers are at the 2- and 5-positions of the pyrrolidine ring at which the side chains are substituted. The third chiral center is introduced in pyrrolidines where the side chain attached to the 5-position is α-hydroxybenzyl.

Compounds with three chiral centers can be obtained as four diastereoisomeric racemates or as eight optical isomers in total. The nomenclature (±)cis erythro, (±)cis threo, (±)trans erythro and (±)trans threo is used to describe individual diastereoisomers.

Embodiments wherein hydrogens at 2- and 5-positions are on the same side of the plane of the pyrrolidine ring are designated "cis". Embodiments where hydrogens at 2- and 5-position are on opposite sides are "trans."

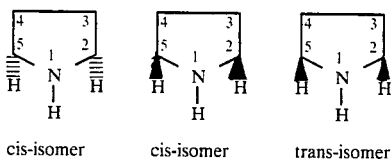

"Erythro/threo" terminology is used to designate the relationship between the configurations of the group attached to the carbon atom bearing the hydroxyl substituent and of the number 5 carbon of the pyrrolidine ring to which it is attached.

"Erythro" indicates those embodiments wherein the hydrogen of carbon atom 5 of the ring and the hydrogen of the hydroxylated carbon occupy the same side of the molecule.

"Threo" indicates those embodiments where the hydrogen of carbon atom 5 of the ring and the hydrogen of the hydroxylated carbon are on the opposite sides of the molecule. For the numbering system, see below.

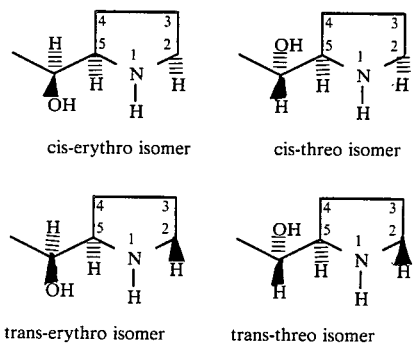

See Stereochemistry of Carbon Compounds, McGraw-Hill, pp. 16–86 (1962); RECUEIL, 83:535, (1964); and Morison and Boyd, Organic Chemistry, 3d Ed., pp. 148–153, (1974).

Numbering on the phenyl rings of the pyrrole or pyrrolidine molecule is illustrated below.

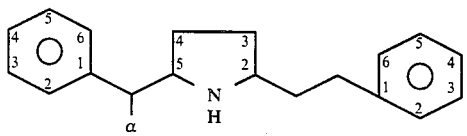

It is to be understood that this invention discloses and encompasses each of the racemates, racemic mixtures, diastereomer and enantiomers.

PREFERRED EMBODIMENTS

Presently preferred embodiments of this invention are compounds of the formula

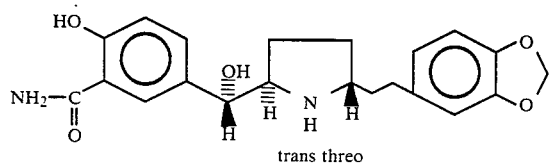

namely, ±trans threo 2-[(3,4-methylenedioxy)phenethyl]-5-[(3-carboxamido-4-hydroxy)-α-hydroxybenzyl]-pyrrolidine.

More preferred embodiments are compounds of the formula

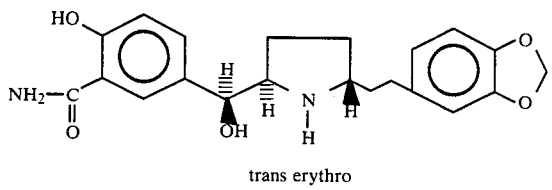

namely, ±trans erythro 2-[(3,4-methylenedioxy)phenethyl]-5-[(3-carboxamido-4-hydroxy)-α-hydroxybenzyl]-pyrrolidine.

Other more preferred embodiments are compounds of the formula

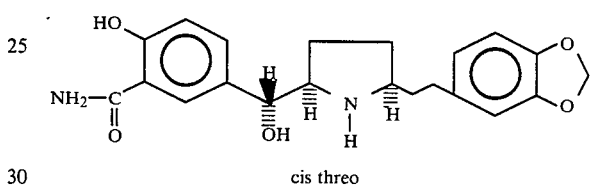

namely, ±cis threo 2-[(3,4-methylenedioxy)phenethyl]-5-[(3-carboxamido-4-hydroxy)-α-hydroxybenzyl]pyrrolidine.

Most preferred embodiments are compounds of the formula

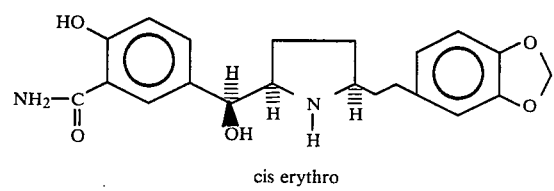

namely, ±cis erythro 2-[(3,4-methylenedioxy)phenethyl]-5-[(3-carboxamido-4-hydroxy)-α-hydroxybenzyl]-pyrrolidine.

PREPARATION PROCEDURES

A compounds of this invention are prepared by the reaction sequence illustrated in Reaction Scheme 1–4. Reaction Scheme 1 illustrates the preparation of ±cis erythro 2-[(3,4-methylenedioxy)phenethyl]-5-[(3-carboxamido-4-hydroxy)-α-hydroxybenzyl]pyrrolidine.

Reaction Scheme 2 illustrates the preparation of ±cis threo 2-[(3,4-methylenedioxy)phenethyl]-5-[(3-carboxamido-4-hydroxy)-α-hydroxybenzyl]pyrrolidine. Reaction Scheme 3 illustrates preparation of ±trans erythro 2-[(3,4-methylenedioxy)phenethyl]-5-[(3-carboxamido-4-hydroxy)-α-hydroxybenzyl]pyrrolidine and Reaction Scheme 4 illustrates preparation of ±trans threo 2-[(3,4-methylenedioxy)phenethyl]-5-[(3-carboxamido-4-hydroxy)-α-hydroxybenzyl]pyrrolidine.

REACTION SCHEME 1
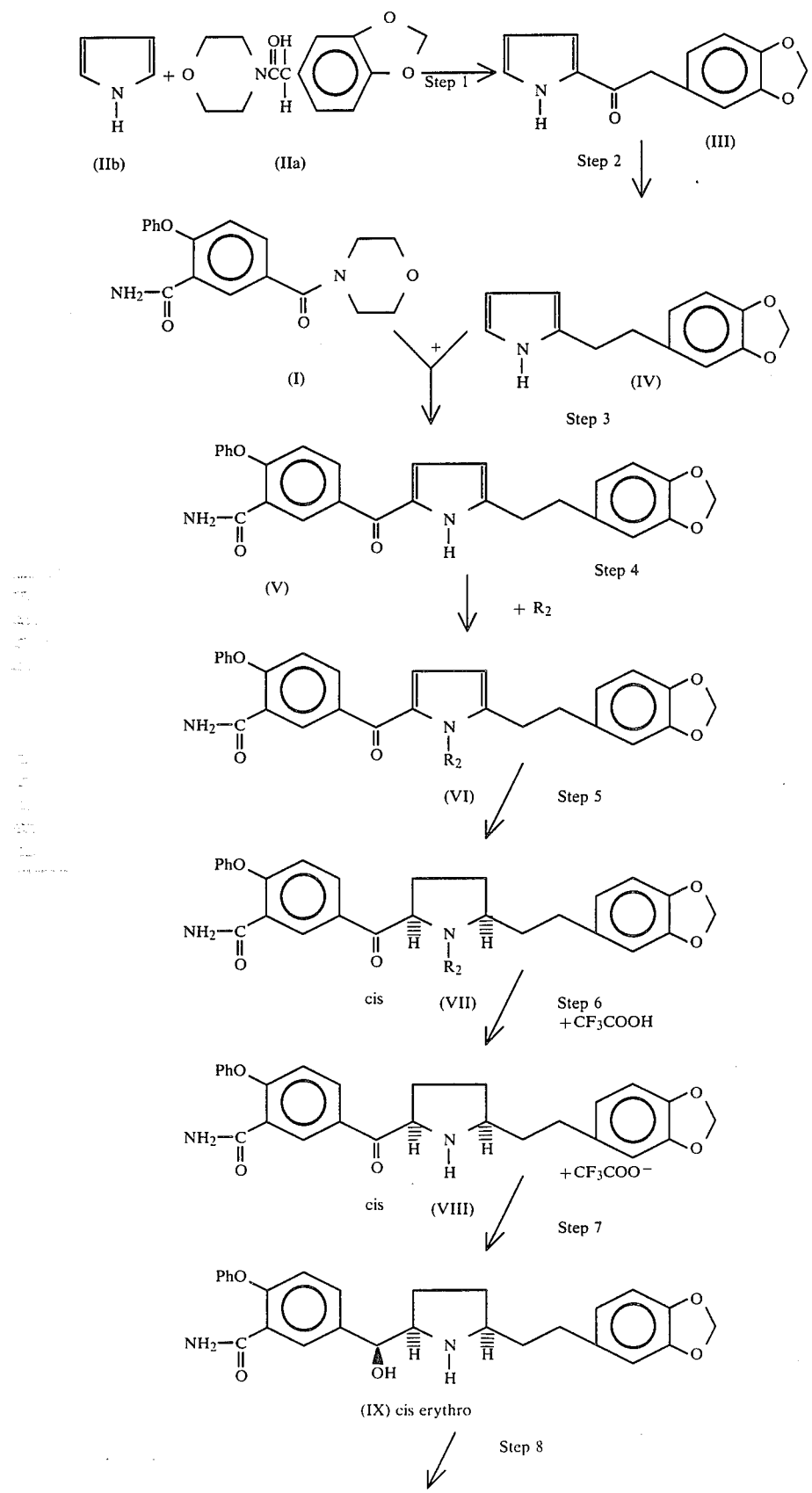

REACTION SCHEME 1 -continued

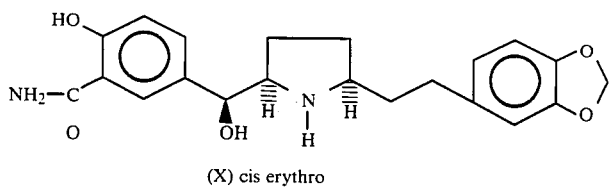

(X) cis erythro

Step 1. Step 1 describes the preparation of 2-[(3,4-methylenedioxy)phenylacetyl]pyrrole (III) from pyrrole (IIb) and [(3,4-methylenedioxy)phenylacetyl]morpholide (IIa).

Pyrrole (IIb) is commercially available from Aldrich. [(3,4-methylenedioxy)phenylacetyl]morpholide (IIa) is prepared by reacting phenylacetic acid with thionyl chloride and with a small amount of dimethylformamide for 10–60 minutes at the temperature of 10°–30° C., preferably at room temperature. The resulting mixture is reacted with morpholine dissolved in an organic solvent, preferably in dry dichloromethane, to give [(3,4-methylenedioxy)phenylacetyl]morpholide (IIa).

[(3,4-methylenedioxy)phenylacetyl]morpholide (IIa) in the presence of an acylating agent, such as acid halides, preferably phosphorous oxychloride, is reacted under the constant stirring for 3–10 hours, preferably for 6 hours. Pyrrole (IIb) dissolved in a chlorinated hydrocarbon solvent, preferably in anhydrous 1,2-dichloroethane, is added. The reaction mixture is stirred for 12–20 hours, alkalized, and purified by methods known in the art to obtain 2-[(3,4-methylenedioxy)-phenylacetyl]pyrrole (III).

Step 2. Step 2 describes the conversion of 2-[(3,4-methylenedioxy)phenylacetyl]pyrrole (III) to 2-[(3,4-methylenedioxy)phenethyl]pyrrole (IV).

Compound (III) is dissolved in an ethereal solvent, preferably dry tetrahydrofuran, and a complex metal hydride, preferably lithium aluminum hydride, is added. The mixture is reacted at reflux temperature for 35–55 hours, preferably 48 hours. Excess of hydride is destroyed with an organic solvent and the reaction mixture is purified by methods known in the art to afford 2-[(3,4-methylenedioxy)phenethyl]pyrrole (IV).

Step 3. Step 3 describes the preparation of 2-[(3,4-methylenedioxy)phenethyl]-5-[(3-carboxamido-4-benzyloxy)benzoyl]pyrrole (V).

[(3-carboxamido-4-benzyloxy)benzoyl]morpholide (I) is prepared from (3-carboxamido-4-benzyloxy)benzoic acid by procedure similar to that of Step 1. (3-carboxamido-4-benzyloxy)benzoic acid, in turn, is prepared from (3-carboxamido-4-hydroxy)benzoic acid which is a known compound of which preparation is described in Brit. Pat. No. 802,841, issued Oct. 15, 1958, in J. Chem. Soc., pp. 4678 (1956), and in Chem. in Industry, pp. 417 (1955)).

It should be noted that in order to prepare ±cis erythro 2-[(3,4-methylenedioxy)phenethyl]-5-[(3-carboxamido-4-hydroxy)benzoyl]pyrrole (X), 4-hydroxy phenolic group of the compounds undergoing reaction steps 3–7, 9–10, 12–14 and 16–17 must be protected. Usually, such protection is achieved with benzylation of phenolic hydroxy group. Therefore, compound I with benzyloxy protecting group must be prepared.

Benzylation of phenolic hydroxy group begins with dissolving methyl ester of (3-carboxamido-4-hydroxy)-benzoic acid in an organic solvent, preferably in dimethylformamide, and treating it with metal hydride, preferably with 1 equivalent of sodium hydride, at a temperature of 10°–30° C., preferably at room temperature. The mixture is stirred until the compounds dissolve, for about 5–6 minutes and benzyl halide, preferably benzyl bromide or chloride is added. The mixture is again stirred at a temperature of 15°–50° until reaction is complete, usually for 1–3 hours. The mixture is purified with methods known in the art and the methyl ester (3-carboxamido-4-benzyloxy)benzoic acid is hydrolyzed with aqueous bicarbonate or carbonate in lower alcohol such as methanol or ethanol to obtain (3-carboxamido-4-benzyloxy)benzoic acid which is then submitted to the same procedure as described in Step 1 to obtain [(3-carboxamido-4-benzyloxy)benzoyl]morpholide (I).

Alternately, the compound (X) may also be prepared from the (3-nitrile-4-hydroxy)benzoic acid. This compound is known and is described in German Patent No. 2,224,681, issued on Oct. 10, 1970, and in corresponding Brit. Applic. 16197-7), published on May 21, 1971.

(3-nitrile-4-hydroxy)benzoic acid is benzylated using the procedure described above for (3-carboxamido-4-hydroxy)benzoic acid and as such, i.e. (3-nitrile-4-benzyloxy)benzoic acid, (3-nitrile-4-benzyloxy)benzoyl and (3-nitrile-4-benzyloxy)α-hydroxybenzyl is carried through the Steps 3–7, 9–10, 12–14 and 16–17. Before debenzylating Steps 8, 11, 15 and 18, a nitrile compound is hydrolyzed to the carboxamido with 10–20% aqueous hydrochloric acid in a polar solvent such as, for example, methanol for about 0,5–5 hours. The nitrile compound can also be hydrolyzed to its corresponding carboxamido compound with 1 equivalent of aqueous sodium hydroxide in a polar solvent.

[(3-carboxamido-4-benzyloxy)benzoyl]morpholide is reacted with an acylating agent, preferably phosphorous oxychloride, at a room temperature for 2–4 hours. Then the compound (IV), dissolved in an organic solvent, preferably in 1,2-dichloroethane, is added and the mixture is stirred for 15–21 hours, preferably for 18 hours. The mixture is purified by methods known in the art to give ±2-[(3,4-methylenedioxy)phenethyl]-5-[(3-carboxamido-4-benzyloxy)benzoyl]pyrrole (V).

Step 4. Step 4 describes the attachment of the protective group $R_2$ to the N atom of the pyrrole compound (V).

Compound (V) is dissolved in a suspension of an ethereal or dipolar solvent, preferably in dry dimethylformamide, and mixed with sodium hydride. The mixture is heated to 45°–60° for 1–3 hours, preferably 2 hours. Suitble N-protecting agent $R_2$, such as aroylchloride, alkanoylchloride, alkylchloroformate, preferably di-t-butylcarbonate, is added and the mixture is stirred at 60°–70° for 1–3 hours. After purification and crystallization by methods known in the art, ±N-protected-2-[(3,4-methylenedioxy)phenethyl]-5-[3-carboxamido-4-benzyloxy)benzoyl]pyrrole, preferably ±1-t-butoxycarbonyl-2-[(3,4-methylenedioxy)phenethyl]-5-[(3-carboxamido-4-benzyloxy)benzoyl]pyrrole (VI) is obtained.

Step 5. Step 5 describes a catalytic reduction of ±1-t-butoxycarbonyl-2-[(3,4-methylenedioxy)phenethyl]-5-[(3-carboxamido-4-benzyloxy)benzoyl]pyrrolidine (VII).

Pyrrole (VI) is reduced in the presence of the noble metal catalyst, such as rhodium on carbon, rhodium on aluminum, platinum oxide, preferably with platinum on carbon, in the solvent or solvent mixture containing lower alcohol, lower alkyl ester or ethereal solvent. The preferred solvent is ethyl acetate. Reduction is carried on under the mild reaction conditions, at the room temperature and pressure of 1–3 atmospheres, preferably at atmospheric pressure for 15–28 hours, preferably for 22 hours. The reduced compound is purified and crystallized by the methods known in the art to give ±cis 1-t-butoxycarbonyl-2-[(3,4-methylenedioxy)phenethyl]-5-[(3-carboxamido-4-benzyloxy)benzoyl]pyrrolidine (VII).

Step 6. Step 6 describes the removal of the N-protecting $R_2$ group from the compound (VII).

A solution of ±cis 1-t-butoxycarbonyl-2-[(3,4-methylenedioxy)phenethyl]-5-[(3-carboxamido-4-benzyloxy)benzoyl]pyrrolidine (VII) in chlorinated hydrocarbon, preferably dry dichloromethane, is added to a strong protic acid, preferably trifluoroacetic acid. The reaction is carried on for 1–3 hours at room temperature. After purification and crystallization by methods known in the art, ±cis 2-[(3,4-methylenedioxy)phenethyl]-5-[(3-carboxamido-4-benzyloxy)benzoyl]pyrrolidine trifuoroacetate (VIII) is obtained.

Step 7. Step 7 describes the reduction of ±cis 2-[(3,4-methylenedioxy)phenethyl]-5-[(3-carboxamido-4-benzyloxy)benzoyl]pyrrolidine trifluoroacetate (VIII) to ±cis erythro 2-[(3,4-methylenedioxy)phenethyl]-5-[(3-carboxamido-4-benzyloxy)-α-hydroxybenzyl]pyrrolidine (IX).

Compound (VIII) is reduced to compound (IX) with a metal borohydride, preferably sodium borohydride dissolved in lower alcohol, preferably in ethanol at 0° temperature. The mixture is reacted for 0.5–3 hours and the solvent is removed. The aqueous residue is diluted with base such as sodium carbonate and the product is extracted with an organic solvent, preferably with ethyl acetate. The extract is washed with water, dried over sodium sulfate, purified, and crystallized by the methods known in the art to give ±cis erythro 2-[(3,4-methylenedioxy)phenethyl]-5-[(3-carboxamido-4-benzyloxy)-α-hydroxybenzyl]pyrrolidine (IX).

Step 8. Step 8 describes the conversion of compound (VIII) in which hydroxy group is protected phenolic hydroxyl, for example benzyloxy, to the compound (X) with unprotected hydroxyl.

The reduction is conducted in alcohol, preferably methanol, in the presence of 5–50 wt% of the noble metal catalyst, preferably 5–20% palladium on carbon. Reduction proceeds at temperatures of 10°–36°, preferably at room temperature, and at atmospheric pressure for 1–100 hours. Purification by methods known in the art and recrystallization from a suitable solvent, preferably acetonitrile, gives compound (X) with unprotected hydroxyl group, namely ±cis erythro 2-[(3,4-methylenedioxy)phenethyl]-5-[(3-carboxamido-4-hydroxy)-α-hydroxybenzyl]pyrrolidine.

Reaction Scheme 2 illustrates preparation of cis threo ±2-[(3,4-methylenedioxy)phenethyl]-5-[(3-carboxamido-4-hydroxy)-α-hydroxybenzyl]pyrrolidine.

REACTION SCHEME 2

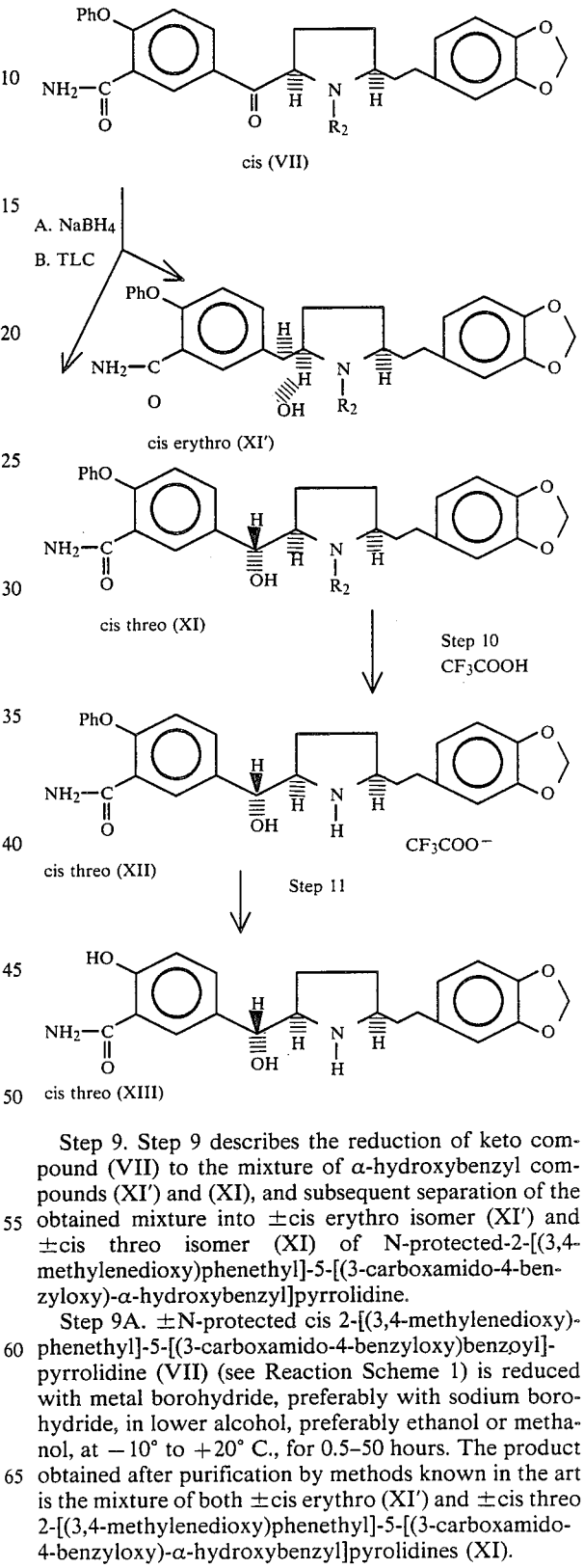

Step 9. Step 9 describes the reduction of keto compound (VII) to the mixture of α-hydroxybenzyl compounds (XI′) and (XI), and subsequent separation of the obtained mixture into ±cis erythro isomer (XI′) and ±cis threo isomer (XI) of N-protected-2-[(3,4-methylenedioxy)phenethyl]-5-[(3-carboxamido-4-benzyloxy)-α-hydroxybenzyl]pyrrolidine.

Step 9A. ±N-protected cis 2-[(3,4-methylenedioxy)phenethyl]-5-[(3-carboxamido-4-benzyloxy)benzoyl]pyrrolidine (VII) (see Reaction Scheme 1) is reduced with metal borohydride, preferably with sodium borohydride, in lower alcohol, preferably ethanol or methanol, at −10° to +20° C., for 0.5–50 hours. The product obtained after purification by methods known in the art is the mixture of both ±cis erythro (XI′) and ±cis threo 2-[(3,4-methylenedioxy)phenethyl]-5-[(3-carboxamido-4-benzyloxy)-α-hydroxybenzyl]pyrolidines (XI).

Step 9B. Obtained mixture of cis erythro and cis threo isomers (XI') and (XI) is separated by thin layer chromatography (TLC), column chromatography, crystallization, or any other common separation technique, preferably by TLC, to obtain ±cis erythro 2-[(3,4-methylenedioxy)phenethyl]-5-[(3-carboxamido-4-benzyloxy)-α-hydroxybenzyl]pyrrolidine (XI') and ±cis threo 2-[(3,4-methylenedioxy)phenethyl]-5-[(3-carboxamido-4-benzyloxy)-α-hydroxybenzyl]pyrrolidine (XI).

Cis erythro compound (XI') is then submitted to Step 6 (Reaction Scheme 1) to remove N-protecting group $R_2$.

Step 10. Step 10 describes the removal of the N-protecting group from ±cis threo 2-[(3,4-methylenedioxy)phenethyl]-5-[(3-carboxamido-4-benzyloxy)-α-hydroxybenzyl]pyrrolidine.

A solution of cis threo compound (XI) in chlorinated hydrocarbons, preferably dichloromethane, is added to a strong protic acid, such as hydrochloric acid or hydrobromic acid, preferably trifluoroacetic acid. The mixture is reacted for 1–50 hours at −10° to +20° C. temperature. The solvent is evaporated and the residue is purified to obtain ±cis threo 2-[(3,4-methylenedioxy)phenethyl]-5-[(3-carboxamido-4-benzyloxy)-α-hydroxybenzyl]pyrrolidine trifluoroacetate (XII).

Step 11. Step 1 describes the debenzylation of compound (XII) wherein hydroxy group is protected phenolic hydroxyl, for example benzyloxy, to the compound (XIII).

The reduction is conducted in alcohol, preferably methanol, in the presence of 5–50 wt% of the noble metal catalyst, preferably 5–20% palladium on carbon. Reduction proceeds at temperatures of 10°–36°, preferably at room temperature, and at atmospheric pressure for 1–100 hours. Purification by methods known in the art and recrystallization from a suitable solvent, preferably acetonitrile, gives compound (XIII) with unprotected hydroxyl group.

REACTION SCHEME 3

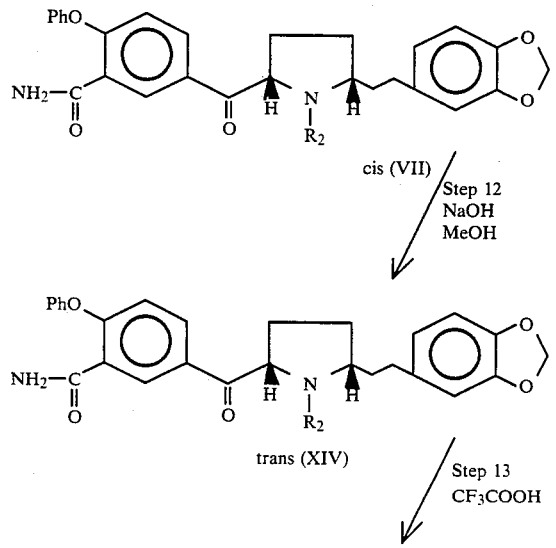

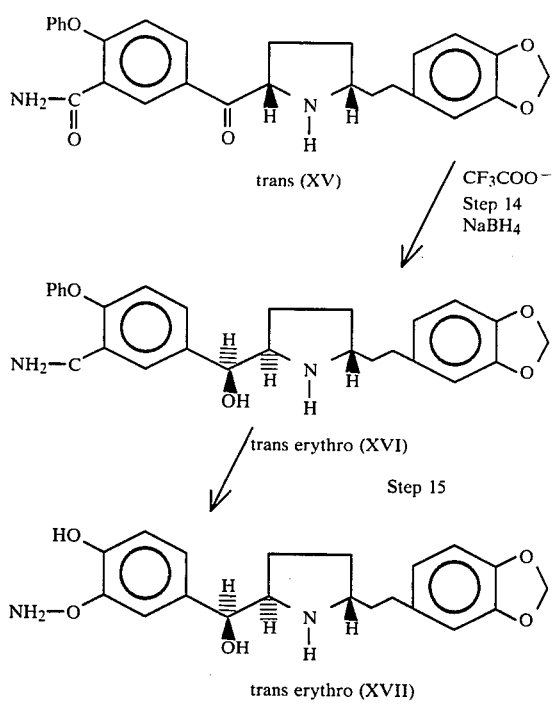

Reaction Scheme 3 illustrates the preparation of ±trans erythro 2-[(3,4-methylenedioxy)phenethyl]-5-[(3-carboxamido-4-hydroxy)-α-hydroxybenzyl]pyrrolidine (XVII).

Step 12. Step 12 illustrates the isomerization of ±cis 2-[(3,4-methylenedioxy)phenethyl]-5-[(3-carboxamido-4-hydroxy)benzoyl]pyrrolidine compound (VII) to the ±trans 2-[(3,4-methylenedioxy)phenethyl]-5-[(3-carboxamido-4-benzyloxy)benzoyl]pyrrolidine compound (XIV).

±Cis-2-[(3,4-methylenedioxy)phenethyl]-5-[(3-carboxamido-4-benzyloxy)benzoyl]pyrrolidine is dissolved in higher alcohol, for example, propanol, butanol, heptanol, pentanol, preferably in t-butanol and potassium in higher alcohol, preferably in t-butanol is added. The mixture is reacted for 1–6 hours, preferably for 2 hours at a temperature of 10°–30°, preferably at room temperature. The mixture is quenched with ammonium salt, preferably with saturated ammonium chloride, poured in the water and extracted with organic solvent, preferably with ethyl acetate, Purification and crystallization of methods known in the art gave the mixture rich in the ±trans isomer 2-[(3,4-methylenedioxy)phenethyl]-5-[(3-carboxamido-4-benzyloxy)benzoyl]pyrrolidine (XIV).

Step 13. Step 13 describes the removal of the N-protecting group from ±trans 2-[(3,4-methylenedioxy)phenethyl]-5-[(3-carboxamido-4-benzyloxy)benzoyl]pyrrolidine.

A solution of trans compound (XIV), is added to a strong protic acid, such as hydrochloric acid or hydrobromic acid, preferably to 1 ml of trifluoroacetic acid cooled on ice. The mixture is reacted for 1 minute to 5 hours at −10° to +20° C. temperature. The solvent is evaporated and the residue is purified to obtain ±trans 2-[(3,4-methylenedioxy)phenethyl]-5-[(3-carboxamido-4-benzyloxy)benzoyl]pyrrolidine trifluoroacetate (XV).

Step 14. Step 14 describes the reduction of ±trans 2-[(3,4-methylenedioxy)phenethyl]-5-[(3-carboxamido-4-benzyloxy)benzoyl]pyrrolidine compound (XV) to ±trans erythro 2-[(3,4-methylenedioxy)phenethyl]-5-[(3-carboxamido-4-benzyloxy)-α-hydroxybenzyl]pyrrolidine (XVI).

±Trans 2-[(3,4-methylenedioxy)phenethyl]-5-[(3-carboxamido-4-benzyloxy)benzoyl]pyrrolidine trifluoroacetate (XV) is reduced with metal borohydride, preferably with sodium borohydride, in a lower alcohol, preferably ethanol or methanol, at −35° to +10° C. The solution is evaporated and the residue is stirred with the solution of an organic solvent, preferably ethyl acetate, and water. The organic layer is evaporated and the residue dissolved in lower alcohol, such as methanol, ethanol, propanol, butanol, preferably in methanol, and acidified with a solution of hydrogen chloride in the same solvent as above, i.e., preferably in methanol to afford ±trans erythro 2-[(3,4-methylenedioxy)phenethyl]-5-[(3-carboxamido-4-benzyloxy)-α-hydroxybenzyl]pyrrolidine compound (XVI).

Step 15. Step 15 describes the debenzylation of compound (XVI) with protected phenolic hydroxyl, for example benzyloxy, to the compound (XVII) where hydroxyl is unprotected.

The reduction is conducted in alcohol, preferably methanol, in the presence of 5–50 wt% of the noble metal catalyst, preferably 5–20% palladium on carbon, in a hydrogen atmosphere. Reduction proceeds at temperatures of 10°–36°, preferably at room temperature, and at atmospheric pressure for 1–100 hours. Purification by methods known in the art and recrystallization from a suitable solvent, preferably acetonitrile, gives compound (XVII) with unprotected phenolic hydroxyl group, namely, ±trans erythro 2-[(3,4-methylenedioxy)phenethyl]-5-[(3-carboxamido-4-hydroxy)-α-hydroxybenzyl]pyrrolidine compound (XVI).

REACTION SCHEME 4

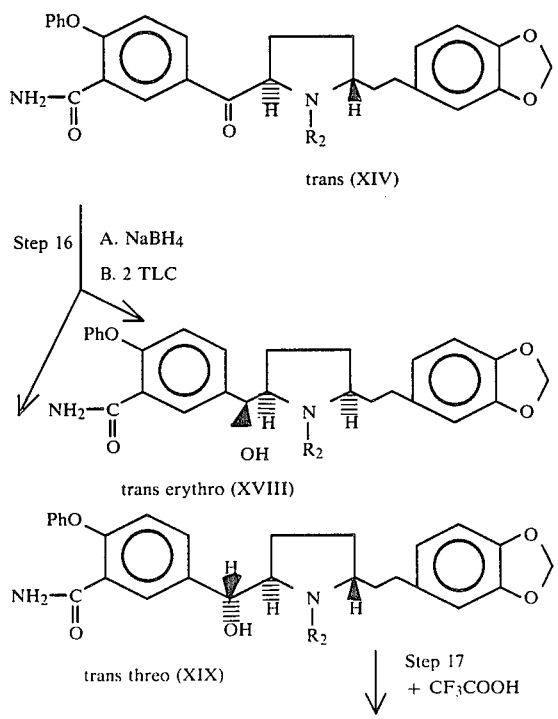

-continued
REACTION SCHEME 4

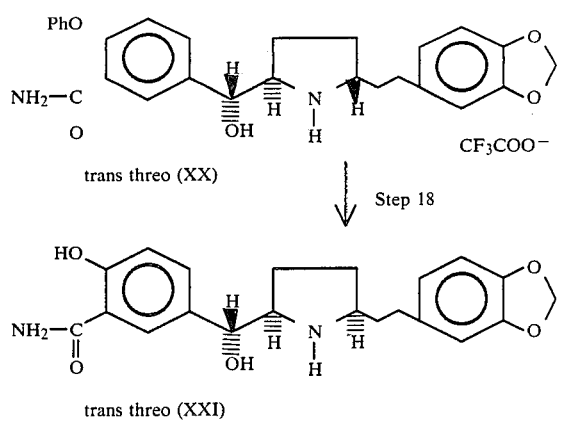

Step 16. Step 16 describes the reduction of N-protected ±trans 2-[(3,4-methylenedioxy)phenethyl]-5-[(3-carboxamido-4-benzyloxy)benzoyl]pyrrolidine compound (XIV) into the N-protected ±trans erythro 2-[(3,4-methylenedioxy)phenethyl]-5-[(3-carboxamido-4-benzyloxy)-α-hydroxybenzyl]pyrrolidine (XVIII) and ±trans threo 2-[(3,4-methylenedioxy)phenethyl]-5-[(3-carboxamido-4-benzyloxy)-α-hydroxybenzyl]pyrrolidine (XIX).

Step 16A. The reaction begins with the reduction of compound (XIV) with metal borohydride, preferably with sodium borohydride, in lower alcohol, preferably ethanol or methanol, at −10° to +20° C. for 0.5–50 hours. The mixture obtained after purification by methods known in the art consist of both ±trans erythro and ±trans threo 2-[(3,4-methylenedioxy)phenethyl]-5-[(3-carboxamido-4-benzyloxy)-α-hydroxybenzyl]pyrrolidine compounds (XVIII) and (XIX).

Step 16B. The mixture obtained in Step 16A is separated by TLC, column chromatography, crystallization or any other common separation technique, preferably by TLC, to obtain ±trans erythro 2-[(3,4-methylenedioxy)-phenethyl]-5-[(3-carboxamido-4-benzyloxy)-α-hydroxybenzyl]pyrrolidine (XVIII) and ±trans threo 2-[(3,4-methylenedioxy)phenethyl]-5-[(3-carboxamido-4-benzyloxy)-α-hydroxybenzyl]pyrrolidine (XIX).

N-protected ±trans erythro 2-[(3,4-methylenedioxy)phenethyl]-5-[(3-carboxamido-4-benzyloxy)-α-hydroxybenzyl]pyrrolidine (XVIII) is submitted to the procedure of Step 13 (Reaction Scheme 3).

Step 17. Step 17 describes the removal of the N-protecting group from the ±trans threo 2-[(3,4-methylenedioxy)phenethyl]-5-[(3-carboxamido-4-benzyloxy)-α-hydroxybenzyl]pyrrolidine compound (XIX).

A solution of ±N-protected trans 2-[(3,4-methylenedioxy)phenethyl]-5-[(3-carboxamido-4-hydroxy)-α-hydroxybenzyl]pyrrolidine compound (XIX) in chlorinated hydrocarbons, preferably dichloromethane, is added to a strong protic acid, such as hydrochloric acid or hydrobromic acid, preferably trifluoroacetic acid. The mixture is reacted for 1–50 hours at −10° to +20° C. temperature. The solvent is evaporated and the residue is purified to obtain the trifluoroacetic acid salt of ±trans threo 2-[(3,4-methylenedioxy)phenethyl]-5-[(3-carboxamido-4-benzyloxy)-α-hydroxybenzyl]pyrrolidine (XX).

Step 18. Step 18 describes the debenzylation of compound (XX) with protected phenolic hydroxyl, for example benzyloxy, to the compound (XXI).

The reduction is conducted in alcohol, preferably methanol, in the presence of 5–50 wt% of the noble metal catalyst, preferably 5–20% palladium on carbon. Reduction proceeds at temperatures of 10°–36°, preferably at room temperature, and at atmospheric pressure for 1–100 hours. Purification by methods known in the art and recrystallization from a suitable solvent, preferably acetonitrile, gives compound (XXI) with unprotected phenolic hydroxyl group, namely ±trans threo 2-[(3,4-methylenedioxy)phenethyl]-5-[(3-carboxamido-4-hydroxy)-α-hydroxybenzyl]pyrrolidine.

ISOLATION, SEPARATION, AND PURIFICATION

Isolation, separation, and purification of the desired final compounds and their intermediates from the reaction mixture can be effected by any suitable separation or purification procedure, such as, for example, extraction, filtration, evaporation, distillation, crystallization, thin-layer chromatography, column chromatography, high pressure liquid chromatography, and the like, or by a combination of these procedures. If not otherwise described above, illustrations of suitable isolation, separation and purification procedures can be had by reference to the Examples herein below. However, other isolation, separation and isolation procedures could, of course, also be used.

In summary, compounds of this invention are prepared by the following steps:

N-protecting ±2-[(3,4-methylenedioxy)phenethyl]-5-[(3-carboxamido-4-benzyloxy)benzyl]pyrrole;

reducing ±N-protected 2-[(3,4-methylenedioxy)phenethyl]-5-[(3-carboxamido-4-benzyloxy)benzoyl]pyrrole with noble metal catalyst under the mild reaction conditions to ±N-protected cis 2-[(3,4-methylenedioxy)phenethyl]-5-[(3-carboxamido-4-benzyloxy)benzoyl]pyrrolidine;

removing N-protecting group from ±cis 2-[(3,4-methylenedioxy)phenethyl]-5-[(3-carboxamido-4-benzyloxy)benzoyl]pyrrolidine;

reducing ±cis 2-[(3,4-methylenedioxy)phenethyl]-5-[(3-carboxamido-4-benzyloxy)benzoyl]pyrrolidine to ±cis erythro 2-[(3,4-methylenedioxy)phenethyl]-5-[(3-carboxamido-4-benzyloxy)-α-hydroxybenzyl]pyrrolidine;

optionally converting ±cis N-protected 2-[(3,4-methylenedioxy)phenethyl]-5-[(3-carboxamido-4-benzyloxy)benzoyl]pyrrolidine to N-protected ±cis threo 2-[(3,4-methylenedioxy)phenethyl]-5-[(3-carboxamido-4-benzyloxy)-α-hydroxybenzyl]pyrrolidine and subsequently removing N-protecting group;

optionally isomerazing N-protected ±cis 2-[(3,4-methylenedioxy)phenethyl]-5-[(3-carboxamido-4-benzyloxy)benzoyl]pyrrolidine to N-protected ±trans 2-[(3,4-methylenedioxy)phenethyl]-5-[(3-carboxamido-4-benzyloxy)benzoyl]pyrrolidine; and subsequently removing N-protecting group and reducing to ±trans erythro 2-[(3,4-methylenedioxy)phenethyl]-5-[(3-carboxamido-4-benzyloxy)-α-hydroxybenzyl]-pyrrolidine;

optionally converting ±trans N-protected 2-[(3,4-methylenedioxy)phenethyl]-5-[(3-carboxamido-4-benzyloxy)benzoyl]pyrrolidine to N-protected ±trans threo 2-[(3,4-methylenedioxy)phenethyl]-5-[(3-carboxamido-4-benzyloxy)-α-hydroxybenzyl]pyrrolidine and subsequently removing N-protecting group;

debenzylating phenolic protected group from ±2-[(3,4-methylenedioxy)phenethyl]-5-[(3-carboxamido-4-benzyloxy)-α-hydroxybenzyl]pyrrolidine (all isomers) to obtain ±2-[(3,4-methylenedioxy)phenethyl]-5-[(3-carboxamido-4-hydroxy)-α-hydroxybenzyl]pyrrolidine;

optionally converting base to a salt; and optionally converting salt to a base.

UTILITY AND ADMINISTRATION

Utility

The compounds of the invention are active antihypertensives. When administered orally or subcutaneously, they relieve hypertension in spontaneously hypertensive rats (SHR) but, at the same time they do not affect rate and force of the heart beat. Accordingly, they are potentially useful as drugs for management of hypertension. They are also active as bronchodilators.

Administration

Administration of the active compounds and salts described herein can be via any of the accepted modes of administration for cardiovascular system regulating agents. These methods include oral or parenteral routes. Parenteral routes include intravenous, subcutaneous, intradermal, or intramuscular administration.

Oral mode of administration is referred for daily administration which is necessary in management of hypertension.

Parenteral route of administration is the administration of drugs to a patient by injection under or through one or more layers of the skin or mucous membrane. Parenteral administration would preferably be reserved for crisis situations, wherein the subject is unable to swallow or administer the medication to himself.

The amount of active ingredient administered will, of course, be dependent on the subject being treated, on the severity of the affliction, on the manner of administration and on the judgment of the prescribing physician. However, an effective dosage is in the range of 0.001–50 mg/kg/day, preferably 0.01–1 mg/kg/day. For an average 70 kg human, this would amount to 0.07–3500 mg per day, preferably 0.7–70 mg/day.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 0.1%–95% active ingredient, preferably 1%–70%.

For parenteral administration, such as, for example, intravenous injections, the compound is dissolved in a vehicle. Vehicle may be, for example, aqueous vehicle, such as sodium chloride injection, Ringer's injection, dextrose injection and others, water miscible vehicle, such as ethyl alcohol, polyethylene glycol of the liquid series or propylene glycol, or nonaqueous vehicles such a corn oil, peanut oil or sesame oil. Vehicle will be buffered to the proper pH in order to stabilize a solution against chemical degradation and formed in such a way as to control isotonicity of injection. Other substances may also be added as antimicrobial or antioxidant agents.

For use as bronchodilators, administration of the active compounds and salts described herein can be via any of the accepted modes for bronchodilation, i.e., any mode described above can be used and compounds may also be administered in aerosol form.

PHARMACEUTICAL COMPOSITION

Depending on the intended mode of administration, the pharmaceutical compositions may be in the form of solid, semi-solid or liquid dosage forms, such as, for example, tablets, pills, capsules, powders, liquids, suspensions, or the like, preferably in unit dosage forms suitable for single administration of precise dosages. The pharmaceutical compositions will include a conventional pharmaceutical carrier or excipient, and a compound of this invention or the pharmaceutically acceptable salt as an active ingredient thereof. In addition, it may include other medicinal or pharmaceutical agents, carriers, adjuvants, etc.

The composition or formulation to be administered will, in any event, contain a quantity of the active ingredient(s) in an amount effective to alleviate the symptoms of the subject being treated.

For solid pharmaceutical compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like. The active ingredient as defined above may also be formulated as suppositories, using as the carrier for example polyalkylene glycols, such as propylene glycol.

Liquid pharmaceutically administerable compositions can be prepared by dissolving or dispersing, or otherwise preparing an active ingredient (as defined above), and mixing it optionally with a pharmaceutical adjuvant in a carrier, such as, for example, water, saline, aqueous dextrose, glycerol, ethanol, and the like, to thereby form a solution or suspension.

If desired, the pharmaceutical composition to be administered may also contain minor amounts of nontoxic auxiliary substances such as wetting or emulsifying agents, pH buffering agents and the like, such as for example, sodium acetate, sorbitan monolaurate, triethanolamine sodium acetate, sorbitan monolaurate, triethanolamine oleate, etc.

Methods of preparing various pharmaceutical compositions with certain amount of active ingredient are known, or will be apparent, to those skilled in this art. For examples, see Remington's Pharmaceutical Sciences, Mack Publishing Company, Easton, Penna., 15th Edition (1975).

EXAMPLE 1

Preparation of
[(3-Carboxamido-4-Benzyloxy)Benzoyl]Morpholide (I)

This example illustrates the preparation of [(3-carboxamido-4-benzyloxy)benzoyl]morpholide. This compound can be prepared from the corresponding [(3-carboxamido-4-hydroxy)benzoic acid by protecting the phenolic hydroxy group.

A. Methyl ester (3-carboxamido-4-hydroxy)benzoic acid was prepared according to the procedure described in *J. Chem. Soc.*, pp. 4678 (1956). The procedure is also described in Brit. Pat. No. 802,841.

B. Methyl ester(3-carboxamido-4-hydroxy)benzoic acid is dissolved in dimethylformamide (10 ml/mmol) and treated with 1 equivalent of sodium hydride at room temperature under constant stirring for about 5 minutes. Then 1 equivalent of benzyl bromide is added and the mixture is stirred at room temperature until reaction is complete, usually for 1 hour. The mixture is poured into water and extracted with ethyl acetate. The extract is washed with water to eliminate dimethylformamide, evaporated in vacuo to afford methyl ester (3-carboxamido-4-benzyloxy)benzoic acid. Methyl ester [(3-carboxamido-4-benzyloxy)benzoic acid is hydrolyzed to benzoic acid with bicarbonate in methanol for about 12 hours to give (3-carboxamido-4-benzyloxy)-benzoic acid.

C. To a suspension of 11.15 g of (3-carboxamido-4-benzyloxy)benzoic acid in 250 ml of dichloromethane was added 2.87 ml of thionyl chloride and 1 ml of dimethylformamide. The mixture is stirred at room temperature for approximately 15 min. or until solution occurred. The solvent was removed in vacuo. The residual acid chloride was dissolved in ether, and 5.8 ml of morpholine was added slowly with stirring. The precipitate was removed by filtration. The ether was evaporated in vacuo to give 11.4 g of an oil which was purified by column chromatography in silica gel with ethyl acetate-hexane (2:3) as the eluting solvent to give in [(3-carboxamido-4-benzyloxy)benzoyl]morpholide (I). (Step 3)

EXAMPLE 2

Preparation of
[(3,4-Methylenedioxy)-Phenylacetyl]Morpholide (IIa)

4 ml of thionyl chloride and 0.5 ml of dry dimethylformamide were added to a solution of 12.5 g of (3,4-methylenedioxy)phenylacetic acid (Trans World Chemical) in 200 ml of dry dichloromethane. The solution was stirred for 15 minutes and evaporated to dryness in vacuo. The residual acid chloride was dissolved in 100 ml of dry dichloromethane. A solution of 5.35 ml of morpholine in 100 of dichloromethane was added dropwise with stirring. When the addition was ended, the mixture was evaporated to dryness in vacuo and the residue was percolated through a short silica gel column using ethyl acetate-hexane (3:7) as the percolating solvent. 13.7 g of [(3,4-methylenedioxy)phenylacetyl]-morpholide (IIa) was obtained. (Step 1)

EXAMPLE 3

Preparation of
2-[(3,4-Methylenedioxy)Phenylacetyl]Pyrrole (III)

Vilsmeier-Haack reaction was carried out according to the method of J. White and G. McGillivray, *J. Org. Chem.*, 42:4248 (1979).

A mixture of 30 g (0.146 mole) of [(3,4-methylenedioxy)phenylacetyl]morpholide and 27 ml (0.295 mole) of phosphorous oxychloride was stirred magnetically at room temperature in a nitrogen atmosphere for 6 h. A solution of 10 ml (0.149 mole) of pyrrole in 700 ml of anhydrous 1,2-dichloroethane was added at a rate such that the temperature did not exceed 30°. The reaction mixture was stirred at room temperature for 18 h. The mixture was cautiously mixed with a solution of 700 ml of 10% sodium carbonate in water and the mixture was heated at reflux temperature with stirring for 1.5 h. The cooled mixture was filtered through celite. The organic phase was separated and combined with dichloromethane extracts (3×500 ml) of the aqueous phase, the organic phases were dried over sodium sulfate and evaporated in vacuo. The residue was subjected to column chromatography over silica gel (1 kg). 2[(3,4-methylenedioxy)phenylacetyl]pyrrole (III) was eluted with dichloromethane and crystallized from acetone-hexane. (Step 1)

EXAMPLE 4

Preparation of
2-[(3,4-Methylenedioxy)Phenethyl]-Pyrrole (IV)

A solution of 6.00 g (0.032 mole) of the 2-[(3,4-methylenedioxy)phenylacetyl]pyrrole (III) in 200 ml of anhydrous tetrahydrofuran was added to a suspension of 600 g (0.153 mole) of lithium aluminum hydride in dry tetrahydrofuran. The mixture was stirred at reflux temperature for 48 h. The mixture was cooled to 0°, and ethyl acetate was cautiously added to destroy the excess hydride. Then the saturated aqueous sodium sulfate was added, the organic phase was decanted, dried over sodium sulfate and evaporated in vacuo. The residue was subjected to column chromatography on neutral alumina (Fluka, Act II). 2-[(3,4-methylenedioxy)phenethyl]pyrrole (IV) was eluted with hexane-ethyl acetate and crystallized from (hexane). (Step 2).

EXAMPLE 5

Preparation of
±2-[(3,4-Methylenedioxy)Phenethyl]-5-[(3-Carboxamido-4-Benzyloxy)Benzoyl]Pyrrole (V)

A mixture of 12,3 g (0.046 mole) of [(3-carboxamido-4-benzyloxy)benzoyl]morpholide (I) (Example 1) and 12 ml (0.13 mole) of phosphorous oxychloride was stirred at room temperature for 3 hours in a nitrogen atmosphere. A solution of 10.0 g (0.058 mole) of 2-[(3,4-methylenedioxy)phenethyl]pyrrole (IV) in 200 ml of dry 1,2-dichloroethane was added and the mixture was stirred at room temperature for 18 h. The reaction mixture was stirred at room temperature for 18 h. The mixture was cautiously mixed with a solution of 700 ml of 10% sodium carbonate in water and the mixture was heated at reflux temperature with stirring for 1.5 h. The cooled mixture was filtered through celite. The organic phase was separated and combined with dichloromethane extracts (3×500 ml) of the aqueous phase, the organic phases were dried over sodium sulfate and evaporated in vacuo. The residue was submitted to column chromatography on neutral alumina (Fluka, Act II). The crude product was purified by column chromatography on silica gel (1 kg). The desired material was eluted with dichloromethane to give ±2-[(3,4-methylenedioxy)phenethyl]-5-(3-carboxamido-4-benzyloxy)benzoyl]pyrrole (V) which was crystallized from dichloromethane-acetone. (Step 3)

EXAMPLE 6

Preparation of
1-t-Butoxycarbonyl-2-[(3,4-Methylenedioxy)Phenethyl]-5-[(3-Carboxamido-4-Benzyloxy)Benzoyl]Pyrrole (VI)

4.10 g (0.012 mole) of ±2-[(3,4-methylenedioxy)-phenethyl]-5-[(3-carboxamido-4-benzyloxy)benzoyl]-pyrrole (V) was added to a 1.40 g of suspension (0.05 mole; 60% dispersion in mineral oil) of sodium hydride in 100 ml of dry dimethylformamide. The mixture was heated at 45°-60° for 2 h. 4.51 g (0.02 mole) of di-t-butyl dicarbonate was added rapidly and the solution was stirred at 60°-70° for 2 h. The reaction mixture was cooled, poured onto ice-water and the product was extracted into ethyl acetate. The extract was washed with water, dried over sodium sulfate and evaporated in vacuo. Then it was purified by column chromatography on alumina (300 g, Fluka, Neutral Act. II). The crude product was crystallized from acetone-hexane to give ±1-t-butoxycarbonyl-2-[(3,4-methylenedioxy)phenethyl]-5-[(3-carboxamido-4-benzyloxy)benzoyl]pyrrole (VI). (Step 4)

EXAMPLE 7

Preparation of ±Cis 1-t-Butoxycarbonyl
2-[(3,4-Methylenedioxy)Phenylethyl]-5-[(3-Carboxamido-4-Benzyloxy)Benzoyl]Pyrrolidine (VII)

A solution of 4.50 g, (0.01 mole) 1-t-butoxycarbonyl-2-[(3,4-methylenedioxy)phenethyl]-5-[(3-carboxamido-4-benzyloxy)benzoyl]pyrrole (VI) in 300 ml of ethyl acetate (2:1) containing 1.8 g of suspended platinum on carbon was hydrogenated at room temperature and atmospheric pressure for 22 hours. The reaction mixture was filtered, the filtrate was evaporated in vacuo and the residue was subjected to column chromatography on neutral alumina (Fluka, Act II). The product was eluted with hexane-ethyl acetate (95:5). The crude ±cis 1-t-butoxycarbonyl 2-[(3,4-methylenedioxy)-phenethyl]-5-[(3-carboxamido-4-benzyloxy)benzoyl]-pyrrolidine (VII) was obtained in quantitative yield as an oil. (Step 5)

The above hydrogenation procedure, however, may result in partial or complete debenzylation of phenolic hydroxyl. If such is the case the phenolic hydroxyl must be again protected by benzylation. The process of benzylation has been described in Example 1.

EXAMPLE 8

Preparation of ±Cis
2-[(3,4-Methylenedioxy)Phenethyl]-5-[(3-Carboxamido-4-Benzyloxy)Benzoyl]Pyrrolidine
Trifluoroacetate (VIII)

50 ml of trifluoroacetic acid was added to a solution of 3.60 g (0.0085 mole) of ±cis 1-t-butoxycarbonyl-2-[(3,4-methylenedioxy)phenethyl]-5-[(3-carboxamido-4-benzyloxy)benzoyl]pyrrolidine (VII) in 200 ml of dry dichloromethane. The reaction solution was stirred at room temperature for 0.5 h. The solvent was removed in vacuo and the residue was crystallized from dichloromethane-ether to give ±cis 2-[(3,4-methylenedioxy)phenethyl]-5-[(3-carboxamido-4-benzyloxy)benzoyl]pyrrolidine trifluoroacetate (VIII). (Step 6)

EXAMPLE 9

Preparation of ±Cis Erythro
2-[(3,4-Methylenedioxy)-Phenethyl]-5-[(3-Carboxamido-4-Benzyloxy)-α-Hydroxybenzyl]Pyrrolidine (IX)

1.35 g (0.035 mole) of sodium borohydride was added to a stirred solution of 2.70 g (0.0057 mole) of ±cis 2-[(3,4-methylenedioxy)phenethyl]-5-[(3-carboxamido-4-benzyloxy)-α-hydroxybenzyl]pyrrolidine in 270 ml ethanol, at 0° temperature. After 1 hour at 0°, the mixture was poured into 100 ml of 10% ammonium chloride solution. The mixture was evaporated in vacuo to remove the ethanol, the residue was cooled to 0°, and 50 ml of a saturated sodium carbonate solution was added. The product was extracted into ethyl acetate, the extract was washed with water, dried over sodium sulfate and evaporated in vacuo. The residue was crystallized from ethyl acetate-hexane to give 1.72 g (93%) of the desired ±cis erythro 2-[(3,4-methylenedioxy)phenethyl]-5-[(3-carboxamido-4-benzyloxy)-α-hydroxybenzyl]pyrrolidine (IX). (Step 7)

EXAMPLE 10

Debenzylation of ±Cis Erythro 2-[(3,4-Methylenedioxy)Phenethyl]-5-[(3-Carboxamido-4-Benzyloxy)-α-Hydroxybenzyl]Pyrrolidine A solution of the ±cis erythro 2-[(3,4-methylenedioxy)phenethyl]-5-[(3-carboxamido-4-benzyloxy)-α-hydroxybenzyl]pyrrolidine (0.600 g 0.0012 mole) in absolute methanol (20 ml) containing suspended 10% palladium on carbon catalyst (0.30 g) was hydrogenated at room temperature and atmospheric pressure for 1 hour. The mixture was filtered through Celite, the filtrate was evaporated in vacuo and the residue was triturated with acetone and crystallized from methanol-acetone, to give ±cis erythro 2-[3,4-methylenedioxy)-phenethyl]-5-[(3-carboxamido-4-hydroxy)α-hydroxybenzyl]pyrrolidine, m.p. 189–191.

Other compounds may be similarly debenzylated:
±trans erythro 2-[3,4-methylenedioxy)phenethyl]-5-[(3-carboxamido-4-hydroxy)α-hydroxybenzyl]pyrrolidine, m.p. 189–191.
±cis threo 2-[3,4-methylenedioxy)phenethyl]-5-[(3-carboxamido-4-hydroxy)α-hydroxybenzyl]pyrrolidine, m.p. 193–193,5.

EXAMPLE 11

A. Preparation of ±Cis Erythro and ±Cis Threo 1-t-Butoxycarbonyl-2-[(3,4-Methylenedioxy)Phenethyl]-5-[(3-Carboxamido-4-Benzyloxy)α-Hydroxybenzyl]Pyrrolidine (XI') and (XI)

A solution of 3.20 g (4.5 mmole) of the ±cis 1-t-butoxycarbonyl-2[(3,4-methylenedioxy)phenethyl]-5-[(3-carboxamido-4-benzyloxy)benzoyl]pyrrolidine (VII), prepared in Example 7 and 6.4 g (16.9 mmole) of sodium borohydride in 300 ml ethanol is heated at a reflux temperature for 45 min. The solvent is removed in vacuo and the residue is partitioned between water and ethyl acetate. The organic phase is evaporated in vacuo and the residue is percolated through a short column of silica gel using ethyl acetate-hexane (1:3) as the percolating solvent.

The resulting mixture is separated by TLC with ethyl acetate/hexane (1:3) into two isomers:
±cis erythro 1-t-butoxycarbonyl 2-[(3,4-methylenedioxy)phenethyl]-5-[(3-carboxamido-4-benzyloxy)-α-hydroxybenzyl)pyrrolidine; and
±cis threo 1-t-butoxycarbonyl 2-[(3,4-methylenedioxy)phenethyl]-5-[(3-carboxamido-4-benzyloxy)-α-hydroxybenzyl]pyrrolidine.

B. Preparation of ±Trans Erythro and ±Trans Threo 1-t-Butoxycarbonyl-2-[(3,4-Methylenedioxy)Phenethyl]-5-[(3-Carboxamido-4-Benzyloxy)α-Hydroxybenzyl]Pyrrolidine (XI') and (XI)

The same procedure as described in Section A is used for the preparation of ±trans erythro (XVIII) and ±trans threo (XIX) compounds shown in Reaction Scheme 4 (Step 16) except that the starting compound is a trans isomer (XIV).

The resulting compounds are:
±trans erythro 1-t-butoxycarbonyl 2[(3,4-methylenedioxy)phenethyl]-5-[(3-carboxamido-4-benzyloxy)-α-hydroxybenzyl]pyrrolidine, m.p. 115°–116°; and
±trans threo 1-t-butoxycarbonyl 2-[(3,4-methylenedioxy)phenethyl]-5-[(3-carboxamido-4-benzyloxy)-α-hydroxybenzyl]pyrrolidine.

EXAMPLE 12

Removal of N-Protecting Group from ±Cis Erythro or ±Cis Threo 1-t-Butoxycarbonyl-2-[(3,4-Methylenedioxy)Phenethyl]-5-[(3-Carboxamido-4-Benzyloxy)-α-Hydroxybenzyl]Pyrrolidine (XI')(XI)

50 ml of trifluoroacetic acid is added to a solution of ±cis erythro 1-t-butoxycarbonyl 2-[(3,4-methylenedioxy)phenethyl]-5-[(3-carboxamido-4-benzyloxy)-α-hydroxybenzyl]pyrrolidine (XI') or to a solution of 3.60 g (0.0085 mol) ±cis threo 1-t-butoxycarbonyl-2-[(3,4-methylenedioxy)phenethyl]-5-[(3-carboxamido-4-benzyloxy)-α-hydroxybenzyl]pyrrolidine (XI) in 200 ml of dichloromethane. The reaction mixture is stirred at room temperature for 0.5–1 hour. The solvent is removed in vacuo and the residue is crystallized from dichloromethane-ether to give trifluoroacetic acid salt of compounds (XI') and (XI).

Resulting compounds are:
±cis erythro 2-[(3,4-methylenedioxy)phenethyl]-5-[(3-carboxamido-4-benzyloxy)-α-hydroxybenzyl]pyrrolidine trifluoroacetate; and
±cis threo 2-[(3,4-methylenedioxy)phenethyl]-5-[(3-carboxamido-4-hydroxy)-α-hydroxybenzyl]pyrrolidine trifluoroacetate (XII). (Step 10)

The same procedure is used for the removal of N-protecting group from compounds (XIV), (XV), (XVIII) and (XIX), shown in Reaction Schemes 3 and 4.

EXAMPLE 13

Isomerization of ±Cis 1-t-Butyloxycarbonyl-2-[(3,4-Methylenedioxy)Phenethyl]-5-[(3-Carboxamido-4-Benzyloxy)Benzoyl]Pyrrolidine to ±Trans-1-t-Butyloxycarbonyl-2-[(3,4-Methylenedioxy)Phenethyl]-5-(3-Carboxamide-4-Benzyloxy)Benzoyl]Pyrrolidine 550 mg of ±cis 1-t-butyloxycarbonyl-2-[(3,4-methylenedioxy)phenethyl-5-[(3-carboxamido-4-benzyloxy)benzoyl]pyrrolidine is dissolved in 50 ml of t-butanol and 1 ml of a solution prepared by dissolving 3–4 g of potassium in 60 ml of t-butanol, is added. After 2 hours at room temperature, the reaction mixture is quenched by adding 1 ml of saturated ammonium chloride. The solution is then poured into water and extracted with ethyl acetate. The ethyl acetate layer is washed, dried and evaporated to yield a residue. The analysis of the residue showed it to be a 50:50 mixture of starting material and a new slightly more polar compound. The more polar compound was isolated by chromatography on silica gel eluting twice with ethyl acetate/hexane (1:2)(2:1) to yield ±trans N-t-butyloxycarbonyl-2-[(3,4-methylenedioxy)phenethyl-5-(3-carboxamido-4-benzyloxy)benzoyl]pyrrolidine, m.p. 115°–116°.

EXAMPLE 14

Conversion of ±Trans 1-t-Butyloxycarbonyl-2-[(3,4-Methylenedioxy)Phenethyl]-5-[(3-Carboxamido-4-Benzyloxy)Benzoyl]Pyrrolidine to ±Trans Erythro 2-[(3,4-Methylenedioxy)Phenethyl]-5-[(3-Carboxamido-4-Benzyloxy)-α-Hydroxybenzyl]Pyrrolidine Hydrochloride 40 mg of ±trans 1-t-butyloxycarbonyl-2-[(3,4-methylenedioxy)phenethyl]-5-[(3-carboxamido-4-benzyloxy)benzoyl]pyrrolidine was dissolved in 1 ml of trifluoroacetic acid cooled on an ice bath. After about 1 minute, the solution was evaporated in vacuo and the residue dissolved in 1 ml of ethanol and added to a solution of 25 mg of sodium borohydride in 5 ml of ethanol cooled to −35°. After warming to room temperature, the solution was evaporated and the residue stirred with ethyl acetate and water. The organic layer was separated, washed, dried, and evaporated to leave a residue which was dissolved in methanol. The solution was acidified with a solution of hydrogen chloride in methanol. The solvent was removed by evaporation and the residue stirred with ethyl acetate to give 28 mg of ±trans erythro-2-[(3,4-methylenedioxy)phenethyl]-5-[(3-carboxamido-4-benzyloxy)-α-hydroxybenzyl]pyrrolidine hydrochloride, m.p. 178°–179°.

EXAMPLE 15

Conversion of ±Trans Erythro 2-[(3,4-Methylenedioxy)Phenethyl]-5-[(3-Carboxamido-4-Benzyloxy)-α-Hydroxybenzyl]Pyrrolidine Hydrochloride to ±Trans Erythro 2-[(3,4-Methylenedioxy)Phenethyl]-5-[(3-Carboxamido-4-Hydroxy)-α-Hydroxybenzyl]Pyrrolidine Hydrochloride 25.9 mg of ±trans erythro 2-[(3,4-methylenedioxy)phenethyl]-5-[(3-carboxamido-4-benzyloxy-α-hydroxybenzyl]pyrrolidine hydrochloride is dissolved in methanol and 3 mg of 5% palladium on carbon catalyst is added. The mixture is stirred overnight in a hydrogen atmosphere. The solution is filtered, the filtrate evaporated and the residue triturated with ethyl acetate. The ±trans erythro-2-[(3,4-methylenedioxy)phenethyl]-5-[(3-carboxamido-4-hydroxy)-α-hydroxybenzyl]pyrrolidine hydrochloride is collected by filtration and dried. After recrystallization from ethanol it had m.p. 189°–190°.

EXAMPLE 16

Conversion of Free Base to Salt Preparation of ±Cis Erythro 2-[(3,4-Methylenedioxy)Phenethyl]-5-[(3-Carboxamido-4-Hydroxy)-α-Hydroxybenzyl]Pyrrolidine Hydrochloride Excess 3% hydrogen chloride in methanol is added to a solution of 1.0 g of ±cis erythro 2-[(3,4-methylenedioxy)phenethyl]-5-[(3-carboxamido-4-hydroxy)-α-hydroxybenzyl]pyrrolidine in 20 ml of methanol. Diethyl ether is added until precipitation is complete. ±Cis erythro 2-[(3,4-methylenedioxy)phenethyl]-5-[(3-carboxamido-4-hydroxy)-α-hydroxybenzyl]pyrrolidine hydrochloride is filtered, washed with ether, air dried and recrystallized.

Other isomers may be similarly converted to various salts.

EXAMPLE 17

Conversion of Salt to Free Base Preparation of ±Cis Erythro 2-[(3,4-Methylenedioxy)Phenethyl]-5-[(3-Carboxamido-4-Hydroxy)-α-Hydroxybenzyl]Pyrrolidine 1.0 l g of ±cis erythro 2-[(3,4-methylenedioxy)phenethyl]-5-[(3-carboxamido-4-hydroxy)-α-hydroxybenzyl]pyrrolidine hydrochloride or trifluoroacetate is dissolved in 50 ml of water. A solution of sodium bicarbonate is added, and the pH adjusted to about pH 5. The resulting free base is extracted with ethyl acetate, the organic layer is then separated, washed twice with water, dried over magnesium sulfate and evaporated to yield ±cis erythro 2-[(3,4-methylenedioxy)phenethyl]-5-[(3-carboxamido-4-hydroxy)-α-hydroxybenzyl)]pyrrolidine as the free base.

EXAMPLE 18

Direct interchange of acid addition salts 1 g of ±cis erythro 2-[(3,4-methylenedioxy)phenethyl]-5-[(3-carboxamido-4-hydroxy)-α-hydroxybenzyl]pyrrolidine hydrochloride, prepared according to Example 13, is dissolved in a solution of 1 ml 50% aqueous sulfuric acid in 10 ml ethanol and the resulting precipitate is harvested. The product is suspended in ethanol and filtered, air dried, and recrystallized from methanol/acetone to yield ±cis erythro 2-[(3,4-methylenedioxy)phenethyl]-5-[(3-carboxamido-4-hydroxy)-α-hydroxybenzyl]pyrrolidine bisulfate.

In Examples 16–23, the active ingredient is ±cis erythro 2-[(3,4-methylenedioxy)phenethyl]-5-[(3-carboxamido-4-hydroxy)-α-hydroxybenzyl]-pyrrolidine hydrochloride.

EXAMPLE 19

| Ingredients | Quantity per tablet, mgs. |
| --- | --- |
| Active ingredient | 25 |
| cornstarch | 20 |
| lactose, spray-dried | 153 |
| magnesium stearate | 2 |

The above ingredients are thoroughly mixed and pressed into single scored tablets.

EXAMPLE 20

| Ingredients | Quantity per tablet, mgs. |
| --- | --- |
| Active ingredient | 100 |
| lactose, spray-dried | 148 |
| magnesium stearate | 2 |

The above ingredients are mixed and introduced into a hard-shell gelatin capsule.

EXAMPLE 21

| Ingredients | Quantity per tablet, mgs. |
| --- | --- |
| Active ingredient | 200 |
| cornstarch | 50 |
| lactose | 145 |
| magnesium stearate | 5 |

The above ingredients are mixed intimately and pressed into single scored tablets.

EXAMPLE 22

| Ingredients | Quantity per tablet, mgs. |
| --- | --- |
| Active ingredient | 108 |
| lactose | 15 |
| cornstarch | 25 |
| magnesium stearate | 2 |

The above ingredients are mixed and introduced into a hard-shell gelatin capsule.

EXAMPLE 23

| Ingredients | Quantity per tablet, mgs. |
| --- | --- |
| Active ingredient | 150 |
| lactose | 92 |

The above ingredients are mixed and introduced into a hard-shell gelatin capsule.

EXAMPLE 24

An injectable preparation buffered to a pH of 7 is prepared having the following composition:

| Ingredients | |
| --- | --- |
| Active ingredient | 0.2 g |
| $KH_2PO_4$ buffer (0.4 M solution) | 2 ml |
| KOH (1 N) | q.s. to pH 7 |
| water (distilled, sterile) | q.s. to 20 ml |

EXAMPLE 25

An oral suspension is prepared having the following composition:

| Ingredients | |
| --- | --- |
| Active ingredient | 0.1 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

EXAMPLE 26

| | |
| --- | --- |
| Active ingredient | 3.0% |
| Span$^R$ 85 (sorbitan trioleate) | 1.0% |
| Freon 11 (trichloromonofluoromethane) | 30.0% |
| Freon 114 (dichlorotetrafluoroethane) | 41.0% |
| Freon 12 (dichlorodifluoromethane) | 25.0% |

EXAMPLE 27

Antihypertensive Activity of ±Cis Erythro 2-[(3,4-Methylenedioxy)Phenethyl]-5-[(3-Carboxamido-4-Hydroxy)-α-Hydroxybenzyl]Pyrrolidine This example illustrates superiod antihypertensive activity of compounds of this invention. In this Example, compounds I and II mean the compounds defined in Table 1.

24 previously trained adult male spontaneously hypertensive rats were distributed into 6 groups (5 animals per group) with approximately equal mean systolic blood pressures. The 6 groups were then studied concurrently in a 2-day compound screening procedure.

Test compounds were randomly assigned to each group. 5 groups received potential antihypertensive agents and 1 control group received vehicle only (water and Tween).

At approximately 17 hours prior to the first day of dosing food was removed from the rat cages. On the morning of Day 1, a group of 4 rats was orally dosed (by gavage) with 6.25 mg/kg, 12.5 mg/kg or 25 mg/kg of ±cis erythro 2-[(3,4-methylenedioxy)phenethyl]-5-[(3-carboxamido-4-hydroxy)-α-hydroxybenzyl)pyrrolidine or other tested compound dissolved/suspended in water (using 2–3 drops Tween 80) with a homogenizer at concentrations such that 0.1 ml of solution was administered per 10 g of body weight. At 4½ hours post dose, food was put back in the cages and the rats were allowed to eat for 2½ hours, after which food was again removed. On the morning of Day 2, rats were orally dosed as described above. Immediately after dosing, the rats were put in restrainers and placed in a heated chamber (30±1.0° C.) for four hours. Normal feeding resumed at the end of the study on Day 2.

Systolic blood pressure (i.e., pressure at the appearance of the first pulse) were recorded using photoelectric transducers. The coccygeal arteries of 3 rats (in a horizontal group) were simultaneously occluded by pump-inflated tail cuffs that were automatically inflated to 300 mmHg and then deflated. A pressure curve and tail pulses were simultaneously monitored on an MFE recorder. Four consecutive (at 30 second intervals) traces were recorded for each rat in a given horizontal group at one, two, three and four hours post compound administration. Subsequent horizontal groups were automatically tested in the same manner.

The mean systolic blood pressure (SBP) of each rat at each observation time was calculated. The SBP of the animals in each dose group were compared to the SBP of the animals in the control group (vehicle only) at each observation time using a one-way analysis of variance test. A compound exhibiting $p \leq 0.05$ at any observation time was considered to exhibit significant antihypertensive activity. Compounds significantly decreasing blood pressure 20 mmHg or more from control values at all four observation times were considered worthy of further examination. In these instances heart rates were calculated and tested for significant change from control heart rate values using the two-tailed test. Pressures were read at hours 1, 2, 3 and 4 after dosing on both days 1 and 2.

A. Table 1 summarizes the results obtained by testing two structurally similar compounds, namely, ±cis erythro 2-[(3,4-methylenedioxy)phenethyl]-5-[(3-carboxamido-4-hydroxy)-α-hydroxybenzyl]pyrrolidine (I) and ±cis erythro 2-[(4-methoxy)phenethyl]-5-[(3-carboxamido-4-hydroxy)-α-hydroxybenzyl]pyrrolidine (II).

TABLE 1

| | | ±cis erythro 2-[(3,4-methylenedioxy)-phenethyl]-5-[(3-carboxamido-4-hydroxy)-α-hydroxybenzyl]pyrrolidine Compound I | | | | | | ±cis erythro 2-[(4-methoxy)phenethyl]-[(3-carboxamido-4-hydroxy)-α-hydroxybenzyl]pyrrolidine Compound II | | | | | |
|---|---|---|---|---|---|---|---|---|---|---|---|---|---|
| | | Test | | | | | | | | | | | |
| | | Systolic Blood Pressure | | | Heart Rates | | | Systolic Blood Pressure | | | Heart Rates | | |
| | | % Δ | P | mm Hg | % Δ | P | BPM | % Δ | P | mm Hg | % Δ | P | BPM |
| | | Dose per os 25 mg/kg | | | | | | Dose per os 25 mg/kg | | | | | |
| Hours Past Dosing | 1 | −54 | 0.05 | −119 | −12 | 0.05 | −40 | −38 | 0.05 | −71 | −2 | NS | −7 |
| | 2 | −42 | 0.05 | −87 | −13 | 0.05 | −41 | −32 | 0.05 | −66 | −5 | NS | −16 |
| | 3 | −40 | 0.05 | −80 | −13 | NS | −37 | −23 | 0.05 | −47 | −14 | 0.05 | −39 |
| | 4 | −40 | 0.05 | −83 | −15 | NS | −43 | −23 | 0.05 | −49 | −15 | 0.05 | −45 |
| | | Dose per os 12,5 mg/kg | | | | | | Dose per os 12,5 mg/kg | | | | | |
| Hours Past Dosing | 1 | −45 | 0.05 | −98 | −13 | 0.05 | −45 | −32 | 0.05 | −54 | −1 | NS | −4 |
| | 2 | −39 | 0.05 | −81 | −14 | 0.05 | −45 | −9 | NS | −15 | ND | ND | |
| | 3 | −32 | 0.05 | −64 | −15 | NS | −41 | −10 | NS | −18 | | | |
| | 4 | −38 | 0.05 | −80 | −30 | 0.05 | −93 | −10 | NS | −17 | | | |

BPM means beats per minute
ΔmmHg means difference in blood pressure expressed in mmHg
% Δ means difference in blood pressure expressed in %
p = significance
NS = not significant
ND = no data available Table 1 illustrates the superiority of compound I ±cis erythro 2-[(3,4-methylenedioxy)phenethyl]-5-[(3-carboxamido-4-hydroxy)-α-hydroxybenzyl]pyrrolidine over compound II ±cis erythro 2-[4-methoxyphenyl]-5-[3-carboxamido-4-hydroxy)-α-hydroxybenzyl]pyrrolidine.

Two dosages, 25 mg/kg and 12,5 mg/kg were tested on spontaneous hypertensive rats to determine their effect on systolic blood pressure and heart beat. At the dosage of 25 mg/kg, both compounds show significant decrease in the systolic blood pressure. However, Compound I is more potent and has longer lasting effect. The decrease in systolic blood pressure persist for the whole testing period of four hours. At the same time heart rates are also decreased. Compound II shows lesser effect on systolic blood pressure and, during the first two hours, does not effect heart rates significantly.

At the lower dosage of 12,5 mg/kg, compound I shows its superiority even more clearly. The decrease in systolic blood pressure is significant and similar, in absolute numbers, to that seen with the higher dose. Again, heart rates are lowered. Compound II, on the other hand, at dosage 12,5 mg/kg decreases the systolic blood pressure only during the first hour. Then, the decrease is small and insignificant.

B. Table 2 summarizes the results obtained by testing four doses of ±cis erythro 2-[(3,4-methylenedioxy)-phenethyl]-5-[(3-carboxamido-4-hydroxy)-α-hydroxybenzyl]pyrrolidine for period of 1–24 hours after gavage. Doses administered using the procedure described above were 50 mg/kg, 25 mg/kg, 12,5 mg/kg and 6,5 mg/kg.

TABLE 2

| | | Compound ±cis erythro 2-[(3,4-methylenedioxy)phenethyl]-5-[(3-carboxamido-4-hydroxy)-α-hydroxybenzyl]pyrrolidine | | | | | |
|---|---|---|---|---|---|---|---|
| | | TEST | | | | | |
| | Hours Past Dosing | Systolic Blood Pressure | | | Heart Rates | | |
| Dose: | | % Δ | P | mm Hg | % Δ | P | BPM |
| 50 mg/kg/per os | 1 | −39 | 0.05 | −76 | — | — | — |
| | 2 | −34 | 0.05 | −65 | −18 | 0.05 | −50 |
| | 3 | −28 | 0.05 | −54 | — | — | — |
| | 4 | −34 | 0.05 | −66 | −21 | 0.05 | −60 |
| | 8 | −28 | 0.05 | −57 | — | — | — |
| | 12 | −7 | NS | −13 | — | — | — |
| | 24 | −10 | 0.05 | −21 | — | — | — |
| 25 mg/kg/per os | 1 | −42 | 0.05 | −82 | — | — | — |
| | 2 | −32 | 0.05 | −61 | −12 | 0.05 | −33 |
| | 3 | −33 | 0.05 | −64 | — | — | — |
| | 4 | −30 | 0.05 | −57 | −20 | 0.05 | −57 |
| | 8 | −17 | 0.05 | −35 | — | — | — |
| | 12 | −3 | NS | −5 | — | — | — |
| | 24 | −8 | NS | −17 | — | — | — |
| 12,5 mg/kg/per os | 1 | −38 | 0.05 | −72 | — | — | — |
| | 2 | −21 | 0.05 | −38 | −8 | — | −23 |
| | 3 | −25 | 0.05 | −51 | — | — | — |
| | 4 | −20 | 0.05 | −38 | −19 | — | −56 |
| | 8 | −9 | NS | −18 | | | |
| | 12 | −7 | NS | −13 | | | |
| | 24 | −14 | NS | −30 | | | |
| 6.25 mg/kg/per os | 1 | −30 | 0.05 | −58 | — | — | — |
| | 2 | −15 | NS | −28 | −10 | — | −12 |
| | 3 | −19 | 0.05 | −38 | — | — | — |
| | 4 | −15 | NS | −29 | −12 | — | −37 |
| | 8 | −1 | NS | −1 | — | — | — |
| | 12 | +9 | NS | +16 | — | — | — |
| | 24 | −11 | NS | −25 | — | — | — |

% Δ, p, ΔmmHg and BPM are as in Table 1.

Table 2 illustrates long-lasting antihypertensive effect of compound ±cis erythro 2-[(3,4-methylenedioxy)- phenethyl]-5-[(3-carboxamido-4-hydroxy)-α-hydroxybenzyl]pyrrolidine.

All tested doses of the above compound are effectively decreasing the systolic blood pressure. Although for the lowest dose (6,5 mg/kg) such decrease is not significant after 2 hours, it reapears again in the 3rd hour.

The dosage 12,5 mg/kg shows significant lowering of systolic blood pressure up to 4 hours after gavage.

At 25 mg/kg dose the compound has extended systolic blood lowering effect which is significant for more than 8 hours.

In dosage 50 mg/kg the lowering of systolic blood pressure can be seen up to 24 hours.

At 12 hours the decrease is insignificant for any tested dosage.

Heart rates are not increased but are overall, mostly significantly, decreased.

From the above it is clear that the compound ±cis erythro 2-[(3,4-methylenedioxy)phenethyl]-5-[(3-carboxamido-4-hydroxy)-α-hydroxybenzyl]pyrrolidine has long-lasting antihypertensive effect. The effect occur without, at the same time, increase in the heart rate. Such increase is an undesirable side effect of many antihyrpertensives which could cause cardiovascular complications and ultimately could lead to heart failure.

What is claimed is:

1. A compound of the formula

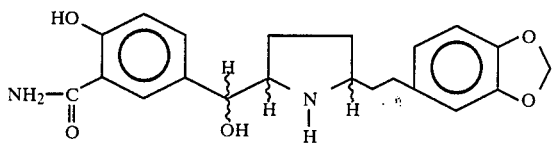

namely, ±2-[(3,4-methylenedioxy)phenethyl]-5-[(3-carboxamido-4-hydroxy)-α-hydroxybenzyl]pyrrolidine and the pharmaceutically acceptable acid addition salts thereof.

2. The compound of claim 1 wherein the compound is a cis isomer.

3. A compound of the formula

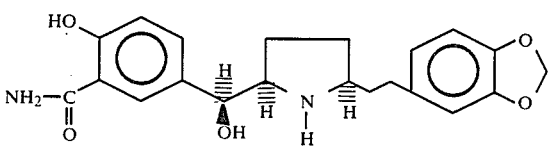

and its enantiomer, namely, (±), (+), and (−) cis erythro 2-[(3,4-methylenedioxy)phenethyl]-5-[(3-carboxamido-4-hydroxy)-α-hydroxybenzyl]pyrrolidine and the pharmaceutically acceptable acid addition salts thereof.

4. A compound of the formula

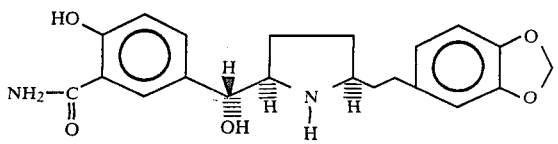

and its enantiomer, namely, (±), (+), and (−) cis threo 2-[(3,4-methylenedioxy)phenethyl]-5-[(3-carboxamido-4-hydroxy)-α-hydroxybenzyl]pyrrolidine and the pharmaceutically acceptable acid addition salts thereof.

5. The compound of claim 1 wherein the compound is a trans isomer.

6. A compound of the formula

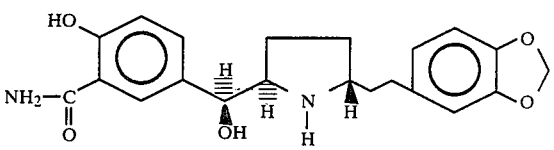

and its enantiomer, namely, (±), (+), and (−) trans erythro 2-[(3,4-methylenedioxy)phenethyl]-5-[(3-carboxamido-4-hydroxy)-α-hydroxybenzyl]pyrrolidine and the pharmaceutically acceptable acid addition salts thereof.

7. A compound of the formula

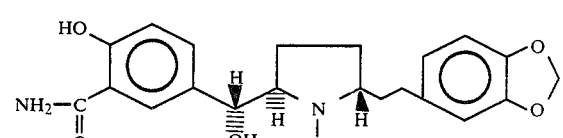

and its enantiomer, namely, (±), (+), and (−) trans threo 2-[(3,4-methylenedioxy)phenethyl]-5-[(3-carboxamido-4-hydroxy)-α-hydroxybenzyl]pyrrolidine and the pharmaceutically acceptable acid addition salts thereof.

8. A pharmaceutical composition which comprises a therapeutically effective amount of a compound of formula

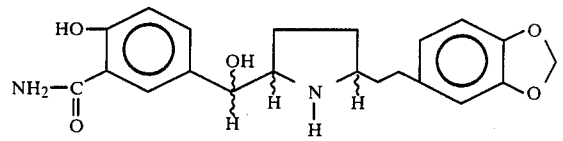

or a pharmaceutically acceptable acid addition salt thereof, in admixture with a pharmaceutically acceptable excipient.

9. A method for regulating hypertension in mammals which method comprises administering to a subject in need of such treatment a therapeutically effective amount of the compound of the formula

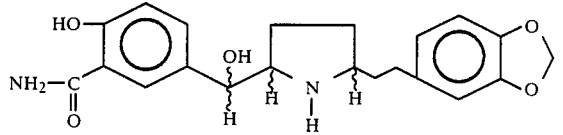

or a pharmaceutically acceptable acid addition salt thereof.

* * * * *